United States Patent
Huth et al.

(10) Patent No.: US 9,456,741 B2
(45) Date of Patent: Oct. 4, 2016

(54) METHOD FOR RAPID CALCULATION OF TEAR FILM LIPID AND AQUEOUS LAYER THICKNESS AND OCULAR SURFACE REFRACTIVE INDEX FROM INTERFEROMETRY SPECTRA

(71) Applicant: Abbott Medical Optics Inc., Santa Ana, CA (US)

(72) Inventors: Stan Huth, Newport Beach, CA (US); Denise Tran, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 5 days.

(21) Appl. No.: 14/298,036

(22) Filed: Jun. 6, 2014

(65) Prior Publication Data

US 2015/0351626 A1    Dec. 10, 2015

(51) Int. Cl.
  *A61B 3/10* (2006.01)
  *G01B 9/02* (2006.01)

(52) U.S. Cl.
  CPC .......... *A61B 3/101* (2013.01); *G01B 9/02* (2013.01)

(58) Field of Classification Search
  CPC ..... A61B 3/1005; A61B 3/101; A61B 3/107
  USPC ..................... 351/205, 212, 246
  See application file for complete search history.

(56) References Cited

U.S. PATENT DOCUMENTS

| | | | |
|---|---|---|---|
| 5,045,704 A | 9/1991 | Coates | |
| 6,236,459 B1 | 5/2001 | Negahdaripour et al. | |
| 6,916,096 B2 | 7/2005 | Eberl et al. | |
| 7,281,801 B2 | 10/2007 | Wang | |
| 7,758,190 B2 | 7/2010 | Korb et al. | |
| 7,866,819 B2 | 1/2011 | Tuan | |
| 7,963,522 B2 | 6/2011 | Hoover | |
| 8,192,026 B2 | 6/2012 | Gravely et al. | |
| 8,585,204 B2 | 11/2013 | Korb et al. | |
| 8,591,033 B2 | 11/2013 | Korb et al. | |
| 8,602,557 B2 | 12/2013 | Huth et al. | |
| 2004/0212781 A1 | 10/2004 | Mihashi et al. | |
| 2006/0109423 A1 | 5/2006 | Wang | |
| 2007/0174014 A1 | 7/2007 | Halm | |
| 2007/0215801 A1 | 9/2007 | Walsh et al. | |
| 2008/0273171 A1 | 11/2008 | Huth et al. | |
| 2009/0201465 A1 | 8/2009 | Huth | |

(Continued)

FOREIGN PATENT DOCUMENTS

WO     2013163367 A1     10/2013

OTHER PUBLICATIONS

Bosch S., et al., "A Method for the Measurement of Reflectances of Spherical Surfaces," Measurement Science and Technology, 1993, vol. 4 (2), pp. 190-192.

(Continued)

*Primary Examiner* — Huy K Mai
(74) *Attorney, Agent, or Firm* — Abbott Medical Optics Inc.

(57) ABSTRACT

A method for determining optical properties of a corneal region. The method includes the steps of obtaining a combined tear film aqueous layer plus lipid layer thickness; obtaining a tear film lipid layer thickness; subtracting the tear film lipid layer thickness from the combined tear film aqueous layer plus lipid layer thickness to obtain a tear film aqueous layer thickness; and determining a corneal layer refractive index based on the tear film lipid layer thickness and the tear film aqueous layer thickness.

14 Claims, 16 Drawing Sheets

(56) References Cited

U.S. PATENT DOCUMENTS

| | | | | |
|---|---|---|---|---|
| 2010/0253907 | A1* | 10/2010 | Korb | A61B 3/0025 351/206 |
| 2013/0141698 | A1 | 6/2013 | Huth et al. | |
| 2013/0169933 | A1 | 7/2013 | Wang | |
| 2013/0229624 | A1* | 9/2013 | Korb | A61B 3/101 351/206 |
| 2013/0293842 | A1 | 11/2013 | Grenon et al. | |
| 2014/0104574 | A1 | 4/2014 | Grenon et al. | |
| 2014/0118699 | A1* | 5/2014 | Huth | A61B 3/101 351/246 |
| 2015/0351627 | A1 | 12/2015 | Huth et al. | |

OTHER PUBLICATIONS

Fogt N., et al., "Interferometric Measurement of Tear Film Thickness By Use of Spectral Oscillations," Journal of Optical Society of America, 1998, vol. 15 (1), pp. 268-275.

Gardner et al., "Tear Film Thickness: Responsiveness to Potential Cognitive Demands", America Academy of Optometry, Tampa Dec. 2004, 1 page.

Geldis et al., "The Impact of Punctual Occulsion on Soft Contact Lends Wearing Comfort and the Tear Film," Eye and Contact Lens, pp. 261-265, 2008, vol. 34 (5).

Goto E., et al., "Computer-Synthesis of an Interference Color Chart of Human Tear Lipid Layer, By a Colorimetric Approach," Investigative Ophthalmology and Visual Science, 2003, vol. 44 (11), pp. 4693-4697.

Goto E., et al., "Differentiation of Lipid Tear Deficiency Dry Eye by Kinetic Analysis of Tear Interference Images," Archives of Ophthalmology, 2003, vol. 121 (2), pp. 173-180.

Hinel E., et al., "Concurrent interferometric Measures of Lipid Layer Thickness and Tear Film Thinning Before and After Application of Lipid Emulsion Drop", American Academy of Optometry, Anaheim Oct. 2008. 1 page.

International Preliminary Report on Patentability and Written Opinion for Application No. PCT/US08/062682, mailed on Nov. 10, 2009, 12 pages.

International Search Report for Application No. PCT/US08/062682, mailed on Nov. 5, 2008, 6 pages.

Kimball et al., Evaporation is the Primary Mechanism of Pre-Corneal Tear Film Thinning [online], Oct. 2008 [retieved on Feb. 25, 2009]. Retrieved from the Internet:< URL: http://www.aaopt.org/Submission/Search/SubmissionViewer.asp"SID=2>.

Kimball et al., Improving Interferometric Tear Thickness Measurements by Using Longer Wavelengths. [online], [retrieved on Feb. 25, 2009]. Retrieved from the Internet:< URL: http://www.aaopt.org/Submission/Search/SubmissionViewer.asp"SID=7>.

King S., et al., "Three Interferometric Methods for Measureing the Thickness of Layers of the Tear Film," Optometry and Vision Science, 1999, vol. 76 (1), pp. 19-32.

King S., et al., "Why does Dry Eye Affect Inferior Cornea More than Superior Cornea", American Academy of Optometry, 2002, pp. 1-2.

King-Smith et al., "In vivo Measurement of the Thickness of Human Corneal Endothelium and Descemets Membrane Using Interferometry, E-Abstract 157," Investigative Ophthalmology & Visual Science, 2002, vol. 43.

King-Smith et al., "Noninvasive Measurement of the Thickness of the Human Corneal Endothelium and Descemet's Membrane", American Academy of Optometry, Dec. 8, 2001, pp. 1-2.

King-Smith et al., "Roughness of the Corneal Surface by Interferometry", Association for Research in Vision and Ophthalmology, May 6, 2007, 1 page.

King-Smith et al., "The Thickness of the Human Precorneal Tear Film. Evidence from Reflection Spectra," Investigative & Visual Science, pp. 3348-3359, 2000, vol. 41 (11).

King-Smith et al., "The Thickness of the Tear Film," Current Eye Research, pp. 357-368, 2004, vol. 29 (4-5), Taylor & Francis Health Sciences.

King-Smith P., et al., Interferometric Analysis of Reflections from the Tear Film and Ocular Surface. [online], [retrieved on Feb. 25, 2009]. Retrieved from the Internet:< URL: http://www.aaopt.org/Submission/Search/SubmissionViewer.asp"SID=4>.

King-Smith P., et al., "Measurement of the Thickness of the Lipid Layer of the Tear Film Using Reflection Spectra," Association for Research in Vision and Ophthalmology, Inc., 2008, Grand Floridian A, Program 1540.

King-Smith P.E., et al., "A Tear Layer of Thickness 1.6 to 7.3 Micrometer Determined from Reflectance Spectra," Investigative Ophthalmology & Visual Science, 1998, vol. 39 (4), pp. 2446-B303.

King-Smith P.E., et al., "Can the Mucus Layer of the Tear Film be Deomstrated by Interferometry", Investigative Ophthalmology & Visual Science, 2004, vol. 45, pp. 1-2.

King-Smith P.E., et al., "Further Evidence that the Thickness of the Normal Human Tear Film is about 3 Micrometre," Investigative Ophthalmology & Visual Science, 2000, vol. 41 (4), pp. 337-B337

King-Smith P.E., et al., "Interferometric Imaging of the Full Thickness of the Precorneal Tear Film," Journal of the Optical Society of America A, Optics, Image Science, and Vision, 2006, vol. 23 (9), pp. 2097-2104.

King-Smith P.E., et al., "Is the Thickness of the Tear Film About 40 Micrometre or About 3 Micrometre", Investigative Ophthalmology & Visual Science, 1999, vol. 40 (4), pp. 2876-B751.

King-Smith P.E., et al., "Measurement of Tear Film Thickness by Spectro-Photometry," Investigative Ophthalmology & Visual Science, 1996, vol. 37 (3), pp. 4984-B594.

King-Smith P.,et al., "Is Inferior Tear Film Thinner than Superior Tear Film", Investigative Ophthalmology & Visual Science, 2003, vol. 44, pp. 2476.

Korb D.R., et al., "Tear Film Lipid Layer Thickness as a Function of Blinking," Cornea, 1994, vol. 13 (4), pp. 354-359.

Korb D.R., et al., "The Effect of Two Novel Lubricant Eye Drops on Tear Film Lipid Layer Thickness in Subjects With Dry Eye Symptoms," Optometry and Vision Science, 2005, vol. 82 (7) , pp. 494-601.

Nichols, et al., "Assessing Visual Parameters in Dry Eye Disease," Cornea and Contact Lens, [retrieved on Feb. 25, 2009]. Retrieved from the Internet:< URL: http://www.aaopt.org/Submissions.Search/SubmissionViewer.asp"SID=2>.

Nichols et al., "Lipid Layer Thickness and Tear Film Thinning Before and After Application of a Lipid Emulsion Drop,," Association for Research in Vision and Ophthalmoogy, 2008, Nichols et al., "Tear Film Thickness and Thinning Rate Following a Six-Week Trial of 2% Diquafosol Tetrasodium vs. Placebo in Dry Eye Patients," 2006.

Nichols et al., "The Impact of Contact Lens Care Solutions on the Thickness of the Tear Film and Contact Lens," Cornea, Clinical Sciences, pp. 825-832, 2005, vol. 24 (7).

Nichols J.J., et al., "Hydrogel Contact Lens Binding Induced by Contact Lens Rewetting Drops," Optometry and Vision Science, 2008, vol. 85(4), pp. 236-240.

Nichols J.J., et al., "Thickness of the Pre- and Post-Contact Lens Tear Film Measured In Vivo by Interferometry," Investigative Ophthalmology & Visual Science. 2003, vol. 44 (1), pp. 68-77.

Nichols J.J., et al., "Thinning Rate of the Precorneal and Prelens Tear Films," Investigative Ophthalmology & Visual Science, 2005, vol. 46 (7), pp. 2353-2361.

Nicols et al., "Role of Lipid Layer as a Barrier to Pre-Lens Tear Film Thinning", American Academy of Optometry, Anaheim Oct. 25, 2008, 1 page.

Scaffidi R.C., et al., "Comparison of the Efficacy of Two Lipid Emulsion Eyedrops in Increasing Tear Film Lipid Layer Thickness," Eye Contact Lens, 2007, vol. 33 (1), pp. 38-44.

Schlote T., et al., "Marked Reduction and Distinct Patterns of Eye Blinking in Patients With Moderately Dry Eyes During Video Display Terminal Use," Graefe's Archive for Clinical and Experimental Ophthalmology. 2004, vol. 242 (4), pp. 306-312.

Schott BK7 Refractive Index Reference, Which is Equivalent to and Replaces Schott Technical Information Document TIE-29. 2005, 17 pages, retrieved from Internet: <URL:http://ltlw3.iams.sinica.edu.tw/support/OpticsGuide/chap04_Material_Properties.pdf>.

(56) References Cited

OTHER PUBLICATIONS

Stenzel O., "The Physics of Thin Film Optical Spectra: An Introduction," in: Springer Series in Surface Sciences, 2005, vol. 44, ERTL G., Eds., Springer-Verlag Berlin Heidelberg, pp. 71-98.

Tiffany J.M., et al., "Refractive Index of Meibomian and Other Lipids," Current Eye Research, 1986, vol. 5 (11), pp. 887-889.

Yap M., "Tear Break-up Time is Related to Blink Frequency," Acta Ophthalmologica, 1991, vol. 69 (1), pp. 92-94.

Zhu H., et al., "A Mathematical Model for Ocular Tear and Solute Balance," Current Eye Research, 2005, vol. 30 (10), pp. 841-854.

International Search Report and Written Opinion for Application No. PCT/US2015/030392, mailed on Oct. 5, 2015, 12 pages.

International Search Report for Application No. PCT/US2015/030385, mailed on Jul. 27, 2015, 3 pages.

* cited by examiner

METHOD FOR RAPID CALCULATION OF TEAR FILM LIPID AND AQUEOUS LAYER THICKNESS AND OCULAR SURFACE REFRACTIVE INDEX FROM INTERFEROMETRY SPECTRA

CROSS-REFERENCE TO RELATED APPLICATIONS

The present application is related to U.S. patent application Ser. No. 14/298,176 to Huth and Tran, "Fast Absolute-Reflectance Method for the Determination of Tear Film Lipid Layer Thickness," filed Jun. 6, 2014, which is incorporated herein by reference in its entirety.

BACKGROUND

The present invention relates to methods for rapid calculation of tear film lipid and aqueous layer thickness and ocular surface refractive index from interferometry spectra.

While a method exists for calculation of parameters such as tear film lipid and aqueous layer thicknesses and ocular surface refractive index using interferometry spectra, this method is relatively slow, requiring many minutes to perform calculations using existing computing platforms. What is needed are improved methods which reduce calculation times using existing computing platforms.

SUMMARY

In one embodiment, the invention provides a method for determining optical properties of a corneal region. The method includes the steps of obtaining a combined tear film aqueous layer plus lipid layer thickness; obtaining a tear film lipid layer thickness; subtracting the tear film lipid layer thickness from the combined tear film aqueous layer plus lipid layer thickness to obtain a tear film aqueous layer thickness; and determining a corneal layer refractive index based on the tear film lipid layer thickness and the tear film aqueous layer thickness.

In another embodiment the invention provides a system for determining optical properties of a corneal region. The system includes a wavelength-dependent optical interferometer and a controller. The controller is in communication with the interferometer and is configured to obtain a combined tear film aqueous layer plus lipid layer thickness, obtain a tear film lipid layer thickness, subtract the tear film lipid layer thickness from the combined tear film aqueous layer plus lipid layer thickness to obtain a tear film aqueous layer thickness, and determine a corneal layer refractive index based on the tear film lipid layer thickness and the tear film aqueous layer thickness.

Other aspects of the invention will become apparent by consideration of the detailed description and accompanying drawings.

DETAILED DESCRIPTION

Figure 1:
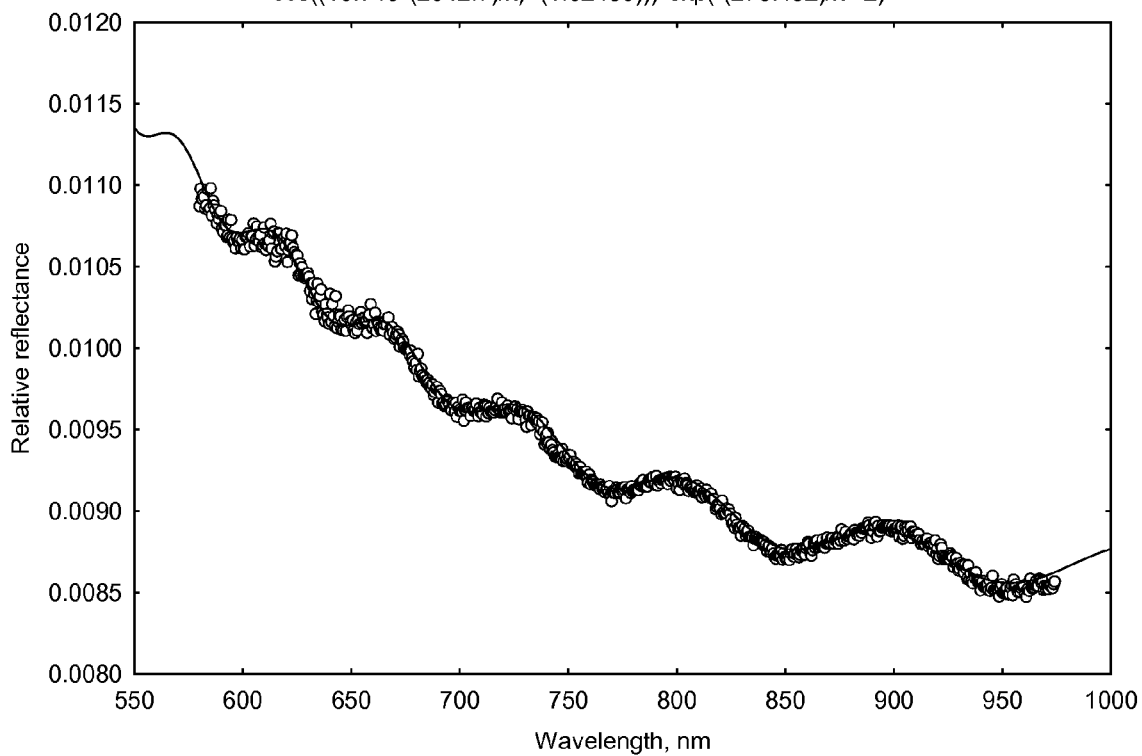
FIG. 1 shows the results of the fitting procedure after using an initial thickness estimate of 3000 nm for the combined 'aqueous+lipid' layer thickness.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The methods disclosed herein offer a significant improvement over existing techniques, including those of the recently-issued patent method (Huth et al., U.S. Pat. No. 8,602,557, hereinafter referred to as the '557 patent; incorporated herein by reference in its entirety). The '557 method takes as long as 475 seconds to complete all calculations for a single interferometry spectrum. This new method requires no more than a few seconds for the calculations, and thus considerably shortens calculation time and also allows one to utilize more interferometry spectra for data analysis, a critical need to provide more statistically robust data and to account for the effects of eye blink dynamics on these tear film parameters. This new method completes all calculations and provides identical results to the method of the '557 patent for lipid and aqueous layer thickness, surface refractive index, fitting error and b and c-terms in seconds (e.g., 10.9 sec. vs. 475 sec.; 3.6 sec. vs. 400 sec.; and 11.8 sec. vs. 408 sec.).

The new methods combine an existing method for 'aqueous+lipid' thickness (Huth et al., U.S. Pat. No. 7,959,293, hereinafter referred to as the '293 patent; incorporated herein by reference in its entirety) with the co-pending method for fast lipid thickness (U.S. patent application Ser. No. 14/298,176), along with the methods in U.S. Pat. No. 8,602,557 for all measurements including lipid and aqueous layer thickness, surface refractive index, fitting error, and b and c-terms. The procedures of the '557 patent are modified by using 'aqueous+lipid' and lipid thickness inputs from the aforementioned fast methods, wherein the lipid thickness value is subtracted from the 'aqueous+lipid' thickness value to obtain an aqueous-only thickness value. As a result, the current calculation matrix of the '557 patent is reduced from a 6×7 matrix (6 aqueous layer thickness starting values and 7 lipid layer thickness starting values for the fitting algorithm) to a single matrix-fitting calculation, thereby reducing the time required for completing all calculations by a factor of approximately $1/(6 \times 7) = 1/42$.

Example 1

The first step in the method of the present invention uses the methods in Huth et al. U.S. Pat. No. 7,959,293, wherein interferometry spectra are produced and relative reflectance data are collected for a series of wavelengths, and wherein v2=relative reflectance and wherein v1=wavelength in nm, and the v1 and v2 data are fit to the following function using a Statistica (StatSoft®, Tulsa, Okla.) software program (Version 7.1, Series 1006b):

$$v2 = -a - b \cdot v1 - c \cdot v1^{}2 + d \cdot (1 + (e/2 \cdot d) \cdot \cos((16.745 \cdot g/v1) + h)) \cdot \mathrm{Exp}(-J/v1^{}2)$$

The Non-linear Estimation method within the Statistica software is used, wherein the equation for v2 above is input as the function to be estimated into the space provided in the user specified regression, least squares module. The Statistica software program uses the Levenburg-Marquardt algorithm to achieve a minimum in the sum of squares of the differences between the interferometer-measured spectrum and a fitted spectrum, fit to the function above, wherein the variables a, b, c, d, e, g, h, and J are iteratively changed. Other mathematical algorithms for fitting data are available within Statistica and other software platforms and can also be employed. This software module requires the number of calculation/fitting iterations to be selected. In one embodiment, 50-300 iterations were found to be acceptable, although in various other embodiments other lower or higher numbers of iterations are also acceptable and can be easily determined by an evaluation of the fit. The program also requires starting values for the variable terms, i.e. a, b, c, d, e, g, h, and J, where the g-term is the initial estimate of the tear film 'aqueous+lipid' layer thickness.

The spectrum in this example was taken from a human subject who was not wearing contact lenses, with the identification number sub21#43. FIG. 1 shows the results of the fitting procedure after using an initial thickness estimate of 3000 nm for the combined 'aqueous+lipid' layer thickness. A result of 2942.7 nm total thickness for the combined 'aqueous+lipid' layer thickness was obtained.

The next step in the method is to calculate the tear film lipid layer thickness. This is calculated using the methods described in co-pending application Ser. No. 14/298,176, using input values for the a-term of 65 nm and for the b-term of 0.66, and the following equation:

$$v6 = ((1 - ((8 \cdot v1 \cdot v2^{}2 \cdot v3)/((v1^{}2 + v2^{}2) \cdot (V2^{}2 + v3^{}2)) + 4 \cdot v1 \cdot v2^{}2 \cdot v3 + ((v1^{}2 - v2^{}2) \cdot (v2^{}2 - v3^{}2)) \cdot (\cos(4 \cdot 3.14159 \cdot v2 \cdot a \cdot 0.98666/v4)))))) \cdot b/v5$$

where the input data are $v6 = R(\lambda)$ meas tear lipid sample (measured % relative reflectance) and wherein $v1 = n_0$ air=1, $v2 = n_1(\lambda)$ tear film lipid (Sellmeier-form), $v3 = n_2(\lambda)$ aqueous, v4=measured $\lambda$ and $v5 = R(\lambda)$ absolute BK7 reference (BK7 absolute R calc)/100 and wherein a Levenberg-Marquardt algorithm is used for fitting the data. The results obtained are shown in Table 1.

TABLE 1

| Level of confidence: 95.0% (alpha = 0.050) | | | | | | |
|---|---|---|---|---|---|---|
| | Estimate | Standard | t-value | p-level | Lo. Conf | Up. Conf |
| a | 31.77767 | 0.130980 | 242.6155 | 0.00 | 31.52055 | 32.03480 |
| b | 0.37007 | 0.000584 | 633.6999 | 0.00 | 0.36892 | 0.37122 |

The value obtained for the a-term, the tear film lipid layer thickness, is 31.78 nm. The calculation of the tear film lipid layer thickness can also be completed in a parallel computer-processing step along with the calculation of the combined 'aqueous+lipid' layer thickness.

Taking the thickness value for the combined 'aqueous+lipid' layer thickness of 2942.7 nm from the first step, the tear film lipid layer-only thickness of 31.78 nm is subtracted and the aqueous-only thickness of 2910.92 nm is obtained. These values for aqueous layer-only thickness and lipid layer-only thickness are input as starting values into the following modified Matlab software program (MATLAB R2013a), taken from U.S. Pat. No. 8,602,557, incorporated herein in its entirety by reference, and modified where indicated.

```
% Program for eye reflectance - Statistica inputs (no variable aqueous or
lipid layer thicknesses)for one spectrum %
% Remarks: b_parameter starting value:1, epithelium refractive index
starting value:1.338+0.00306.*(1000./L).^2
%---------------------------------------------------------------------
-----------------------------------------%
% Aqueous layer thickness from Statistica
At=2910.92% Excel read
excl=xlsread('sub21#43.xls');
%----------------j1__25min__-------------------------------------------
------------------------------------------%
% Parameters
At=At; ('557 program line: At=At−50)
z2=0;
% Plot of exp. data
plot(excl(:,1),excl(:,2))
L=[excl(:,1)];
R=[excl(:,2)];
hold on
% Loops
for y=0 ('557 program line: y = 0:20:100)
z2=z2+1;
z=0;
% Input lipid thickness from Statistica (no semi-colon or punctuation at
% end)
for p=31.78 ('557 program line: p = 20:20:140)
```

The remaining program code is identical to that in U.S. Pat. No. 8,602,557.

The following results were obtained in 7.8 seconds with an IBM ThinkPad computer with an Intel® Core™ 2 Duo CPU, T9400@2.53 GHz (1.59 GHz, 1.98 GB of RAM):

Lipid layer thickness: 35.1 nm
Aqueous layer thickness: 2969.5 nm
Corneal surface refractive index: 1.3360
b-term: 0.3760
c-term: 0.0560
error: 2.96e−6

Figure 2:
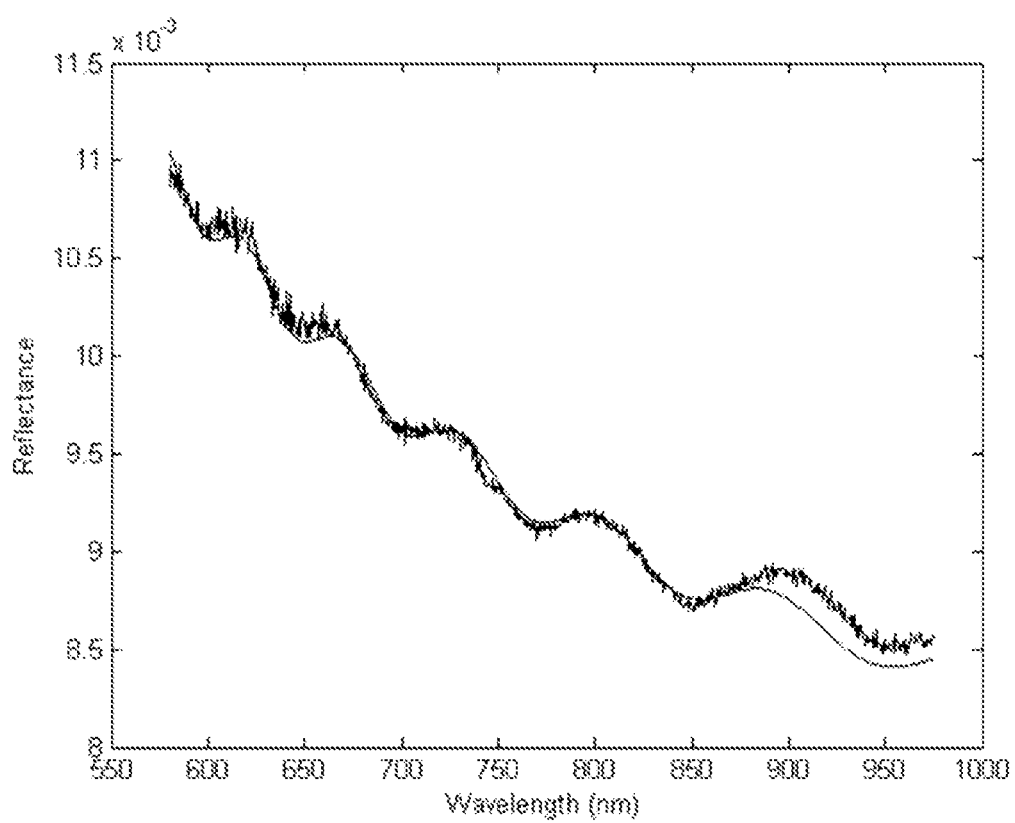
FIG. 2 shows results of a curve-fitting procedure using the presently-disclosed methods.
Figure 3:
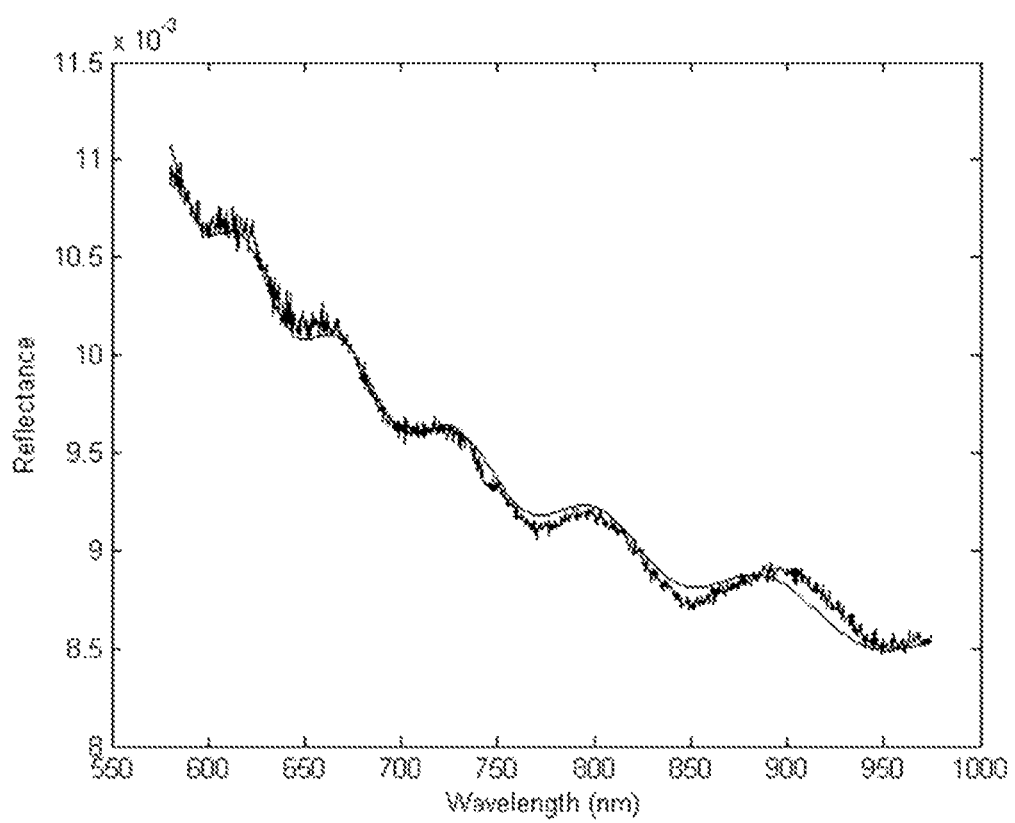
FIG. 3 shows results of a curve-fitting procedure with the same data as in FIG. 2 using the methods of the 557 patent.

FIG. 2 shows the fit of the results (smooth line) to the original spectrum (jagged line), based on data from subject sub21#43. The parameter results were identical to those obtained with the program code in U.S. Pat. No. 8,602,557, which took 131 seconds to run on the same computer with the same data set (i.e. from subject sub21#43). The fit obtained in FIG. 2 with the method of the present invention is substantially the same as that obtained with the method in U.S. Pat. No. 8,602,557 (FIG. 3).

Example 2

The method of Example 1 was followed with analysis of an interferometry spectrum taken from a human subject, identification number RHlf8 hr#20, wearing Acuvue 2® soft contact lenses.

The Statistica results were 1572.15 nm for the combined tear film 'aqueous+lipid' layer thickness and 31.53 nm for the tear film lipid layer thickness, giving 1540.60 nm for the tear film aqueous layer thickness. As with Example 1, in the present Example 2 the tear film aqueous and lipid layer thickness values were input as starting values into the revised Matlab software program. The substrate surface underlying the tear film in this case was the contact lens surface, rather than the corneal epithelium as in Example 1. Thus, the surface refractive index starting value for the Matlab software program was the published value for the bulk contact lens, 1.4055. It was determined, however, that using refractive index starting values of 1.338, 1.37, 1.4055, and 1.42 all gave identical results. Thus, the nominal refractive index starting value for the corneal epithelium, 1.338, can also be used for tear film spectra from contact lens wearers. Table 2 lists the following results, which were obtained in 3.1 seconds with the method of the present invention, compared to 467 seconds with the method in the '557 patent.

TABLE 2

| Parameter | present invention | '557 method |
|---|---|---|
| Lipid layer thickness, nm | 56.5 | 63.5 |
| Aqueous layer thickness, nm | 1507.6 | 1502.0 |
| Lens surface refractive index | 1.3649 | 1.3663 |
| b-term | 0.0297 | 0.0268 |
| c-term | 0.3940 | 0.3858 |
| Error | 1.02E−07 | 9.81E−08 |
| Calculation time, seconds | 3 | 467 |

Figure 4:
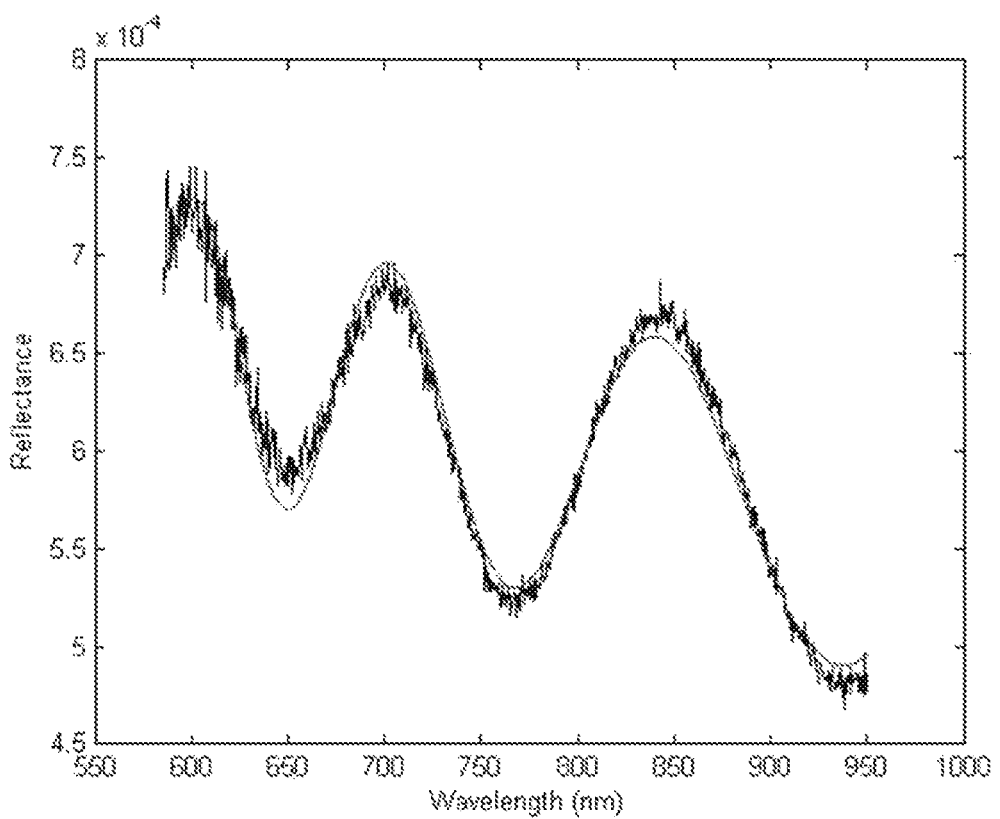
FIG. 4 shows results of a curve-fitting procedure using the presently-disclosed methods.
Figure 5:
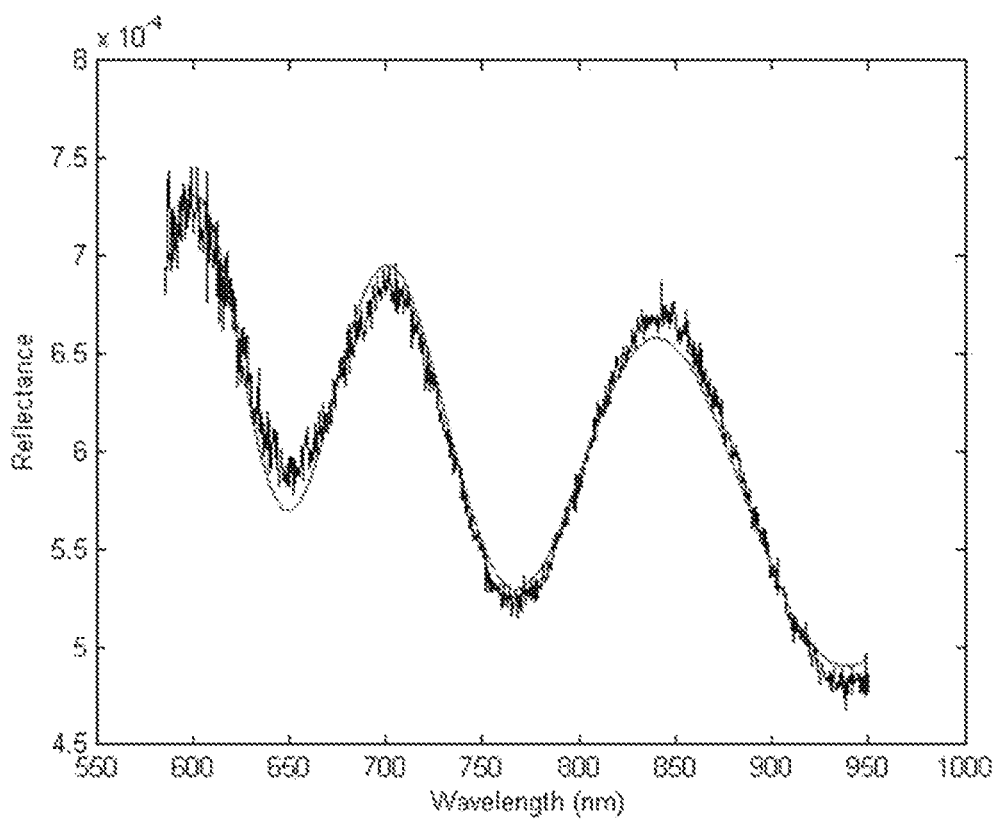
FIG. 5 shows results of a curve-fitting procedure with the same data as in FIG. 4 using the methods of the '557 patent.

The results above and fit obtained in FIG. 4 with the method of the present invention are very close to that obtained with the slower methods of U.S. Pat. No. 8,602,557 (FIG. 5) using the same data set (both of FIGS. 4 and 5 use data from subject RHlf8 hr#20).

Example 3

The method of Example 1 was followed with interferometry spectra taken from six additional subjects, none of whom was wearing contact lenses. Results are shown in Table 3. Interferometry spectra from four subjects, with identification numbers sub1#29, sub4#5, sub6#7, and sub6base#84 produced the same results for the method of the present invention as with the methods of the '557 patent. Calculation times for all four spectra were much shorter with the method of the present invention, ranging from 2.2-11.8 sec, compared to 137-408 sec for the methods of the '557 patent. Note in Table 3 that the methods of the '557 patent consistently produced longer calculation times than the method of the present invention, although different times on occasion when the calculations were repeated. It was noted that the program tended to run faster after the first calculation for the particular day.

Figure 6:
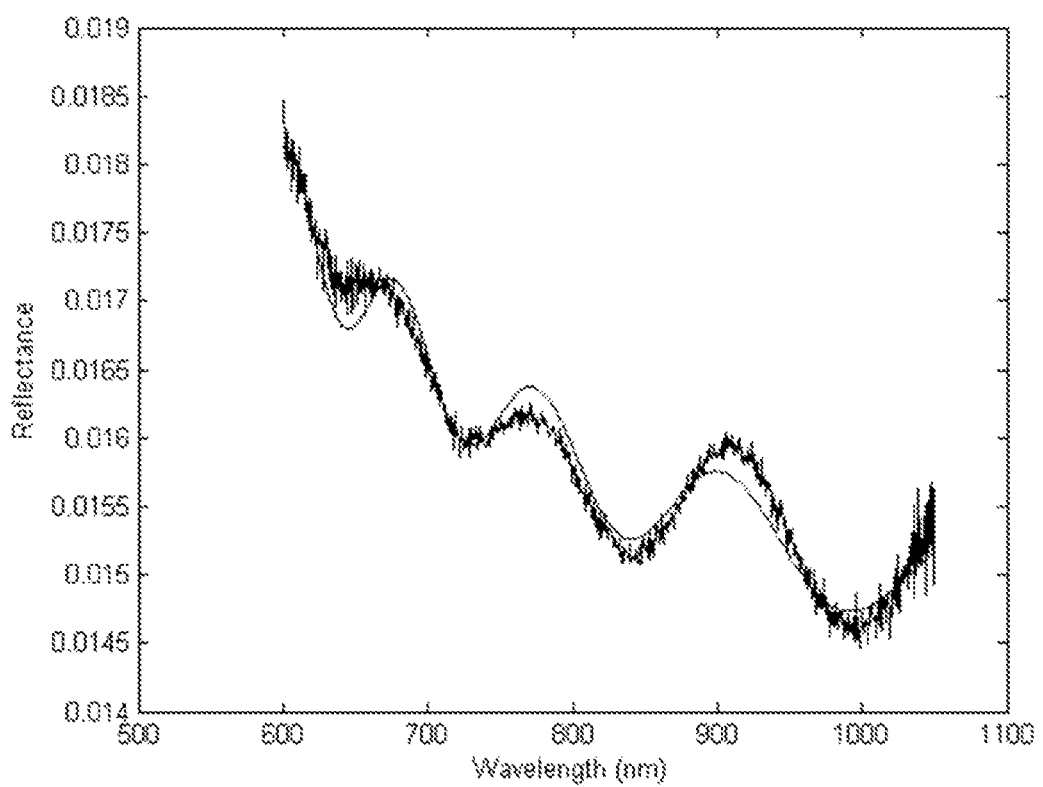
FIG. 6 shows results of a curve-fitting procedure using the presently-disclosed methods.
Figure 7:
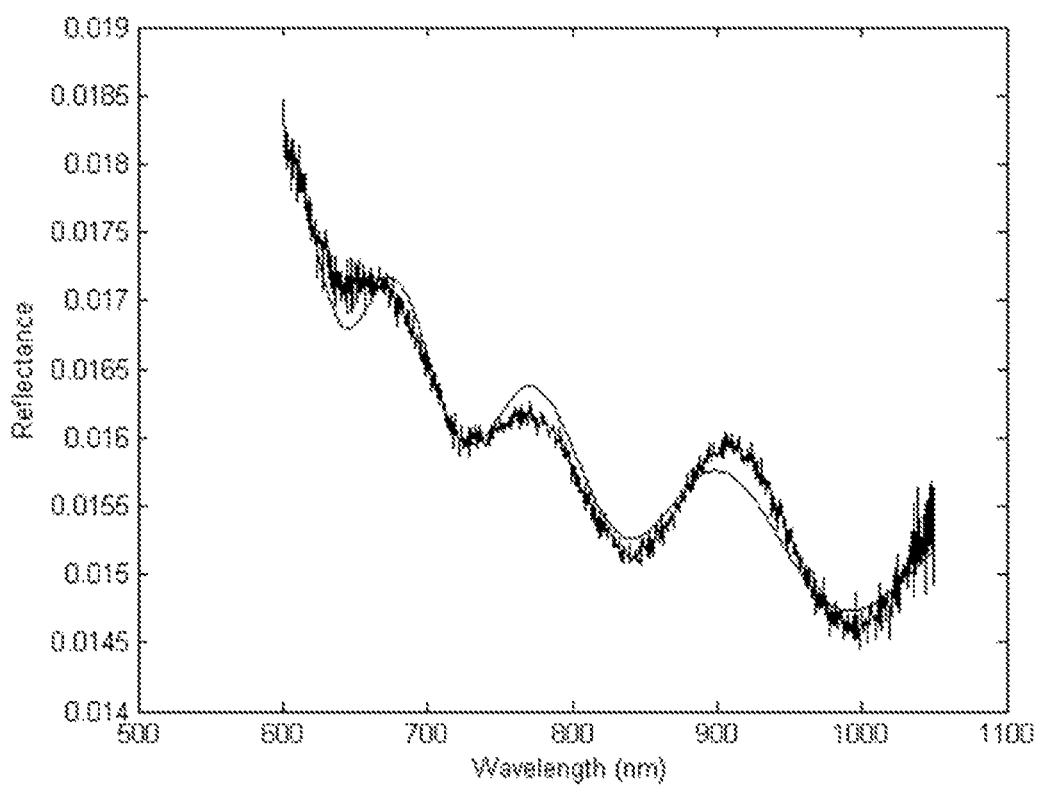
FIG. 7 shows results of a curve-fitting procedure with the same data as in FIG. 6 using the methods of the '557 patent.

FIGS. 6 and 7 show analyses of data for subject sub4#5 using the methods of the present invention and of the '557 patent, respectively. The fits and results are essentially identical, but the calculation times are 3.8 vs. 235 seconds, respectively. The remaining three subjects and four spectra, with identification numbers sub2DE, sub3#15, sub3#56, and sub12#93, produced close results for the method of the present invention compared to the methods of the '557 patent.

Figure 8:
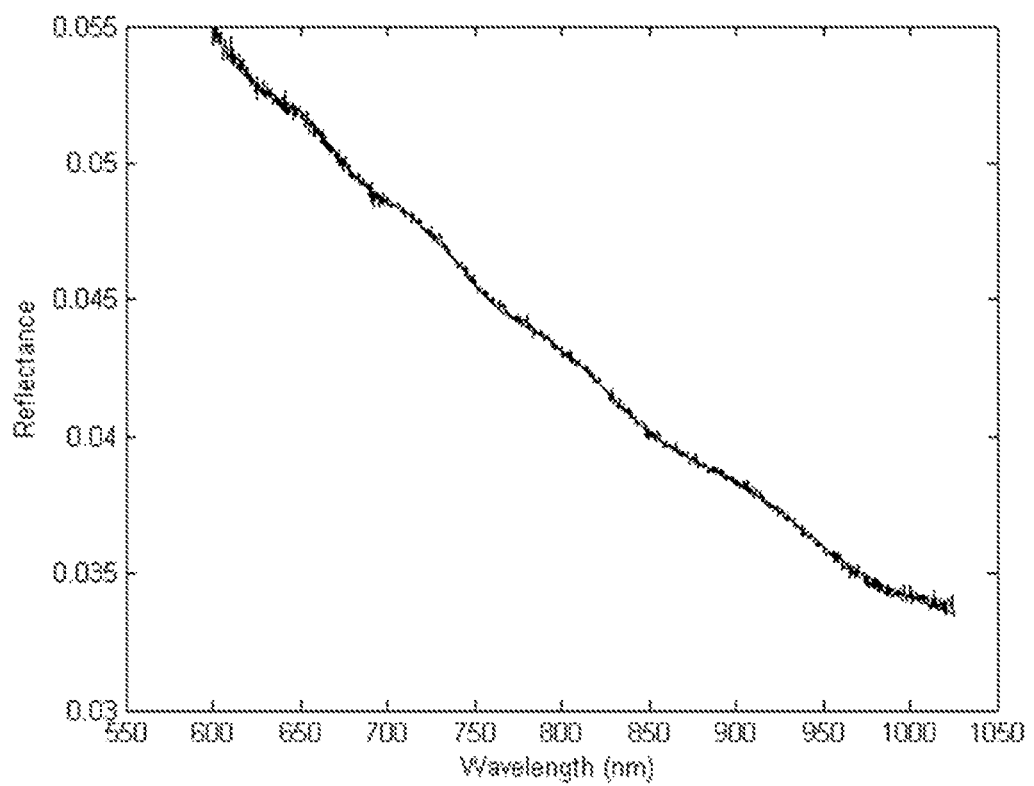
FIG. 8 shows results of a curve-fitting procedure using the presently-disclosed methods.
Figure 9:
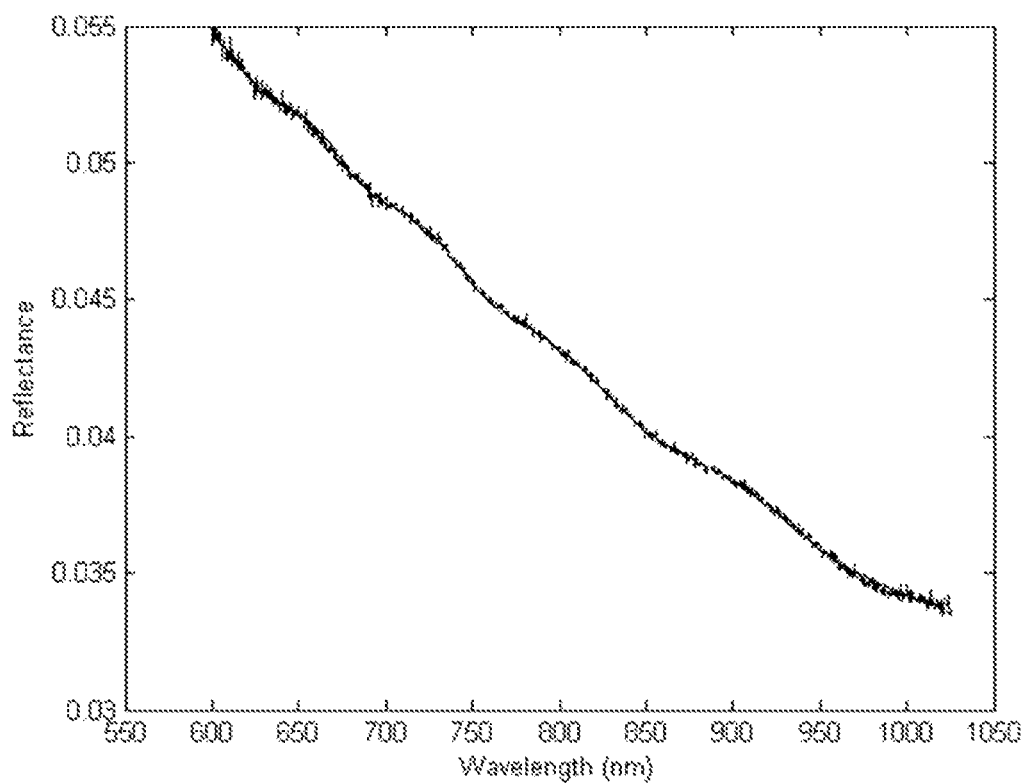
FIG. 9 shows results of a curve-fitting procedure with the same data as in FIG. 8 using the methods of the '557 patent.

FIGS. 8 and 9 show spectrum sub2DE analyses with the method of the present invention and the methods of the '557 patent, respectively. The very low tear film aqueous layer reflectance interference oscillation amplitude in this spectrum makes the analysis challenging, which required 400 seconds with the methods of the '557 patent, whereas the present methods achieved a fit in only 3.8 seconds.

Figure 10:
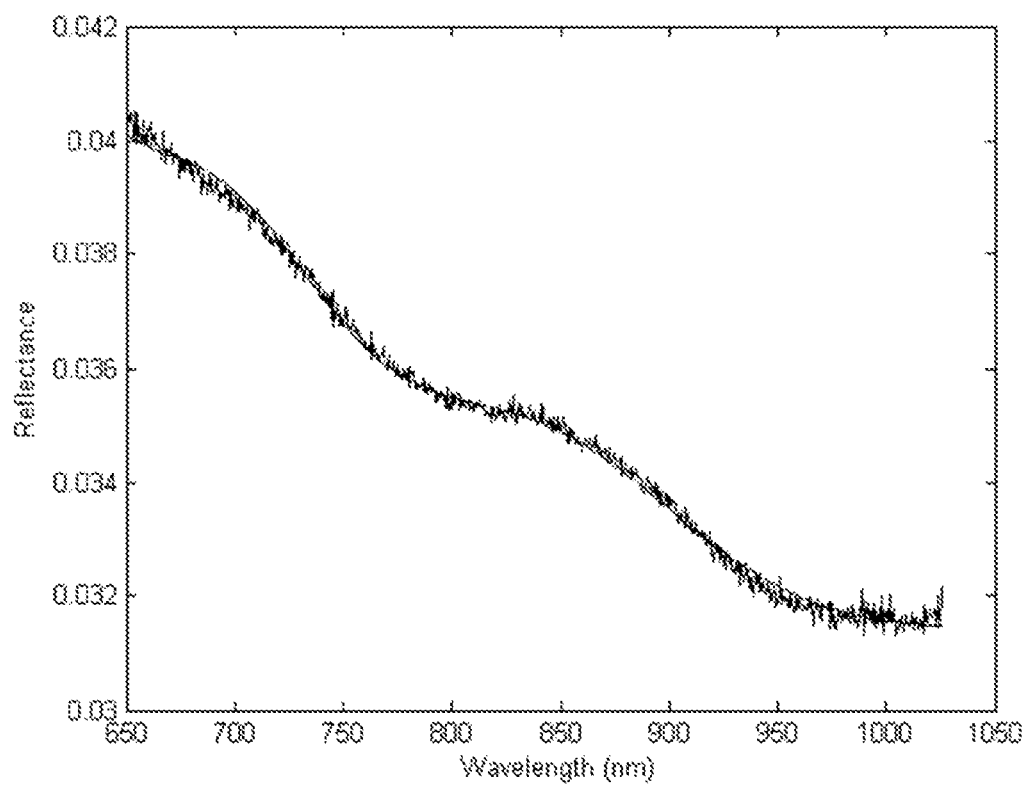
FIG. 10 shows results of a curve-fitting procedure using the presently-disclosed methods.
Figure 11:
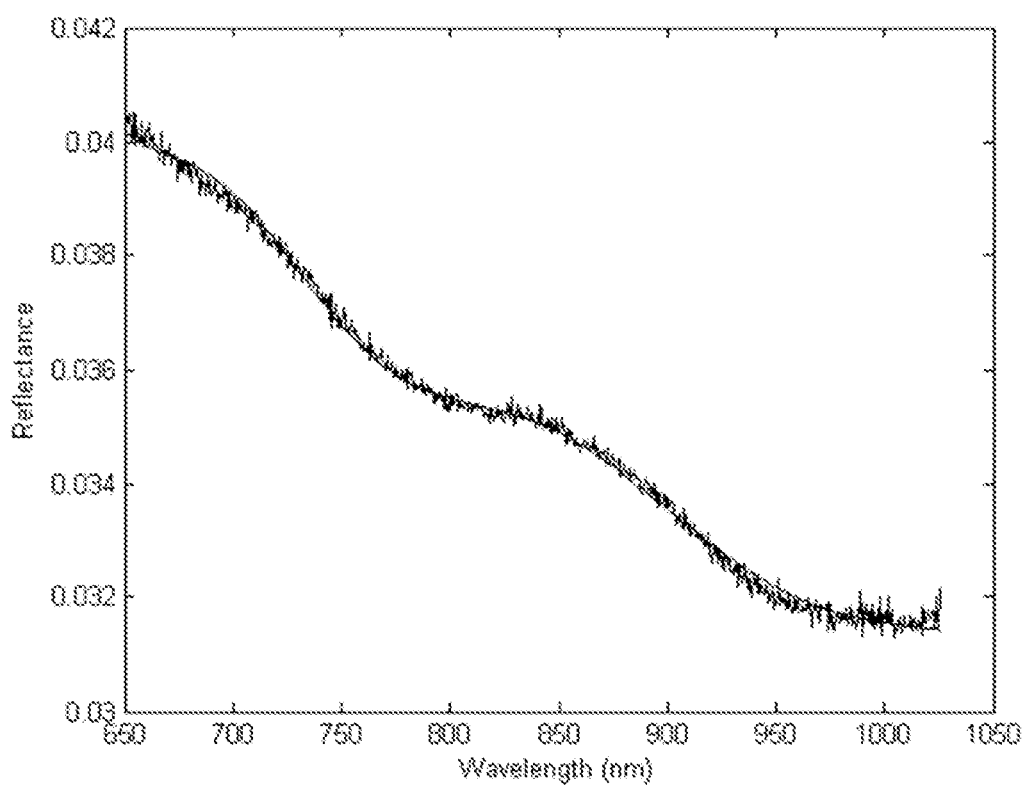
FIG. 11 shows results of a curve-fitting procedure with the same data as in FIG. 10 using the methods of the '557 patent.

FIGS. 10 and 11 show spectrum sub3#56 analyses with the method of the present invention and the methods of the '557 patent, respectively. Table 3 shows that the original tear film lipid layer thicknesses derived from the Statistica program, which are used as input values for the present Matlab software program, are close, but different from the resulting Matlab program calculated thicknesses derived from the spectrum fits. Table 3 also shows that the present method produced closer lipid layer thickness values to those obtained from the Statistica program in those cases in which results between the methods of the '557 patent and the present methods differ.

Figure 12:
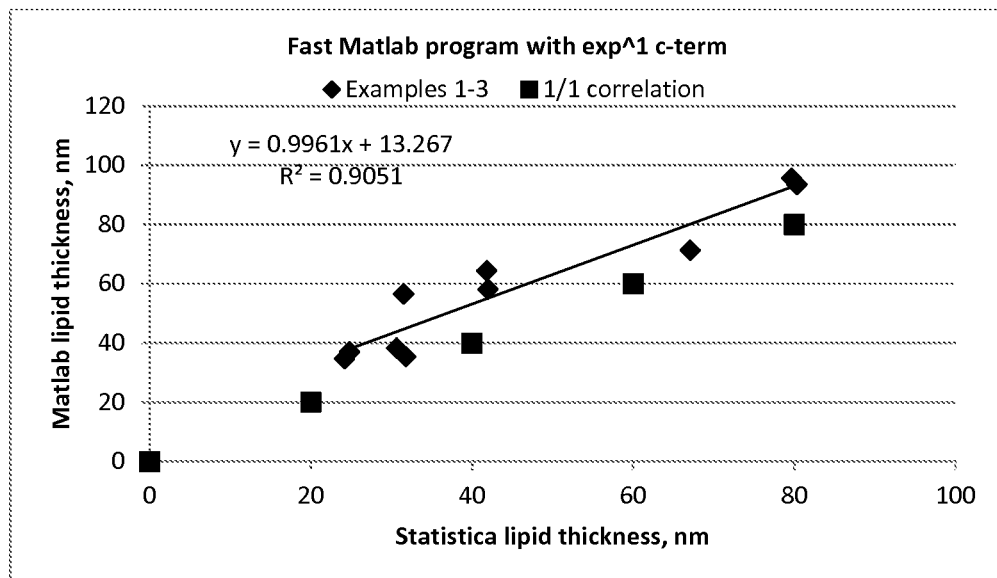
FIG. 12 shows the correlation between the tear film lipid layer thickness values obtained using the tear film lipid layer thickness values using the methods from co-pending application Ser. No. 14/298,176 and those obtained using the presently-disclosed methods for the data from Examples 1-3.

FIG. 12 shows the correlation between the tear film lipid layer thickness values obtained using the tear film lipid layer thickness values using the methods from co-pending application Ser. No. 14/298,176 and those obtained using the presently-disclosed Matlab method lipid layer thickness values for spectra from Examples 1-3. A reasonably good correlation was found (slope=0.9961, intercept 13.267 nm and $r^2=0.9051$) given the nanometer measurement scale for the clinical interferometer and associated mathematics and software. The average difference found was 13 nm, which is considered good. Differences are expected due to the more rigorous calculations required for the Matlab software program, which calculates tear film aqueous and lipid layer thicknesses and either corneal surface or contact lens surface refractive indices. It can be seen from Table 3 that the differences become small as the tear film aqueous layer thickness increases, likely due to the better spectrum fits which can be obtained with additional aqueous layer thickness reflectance interference oscillations.

Figure 13:
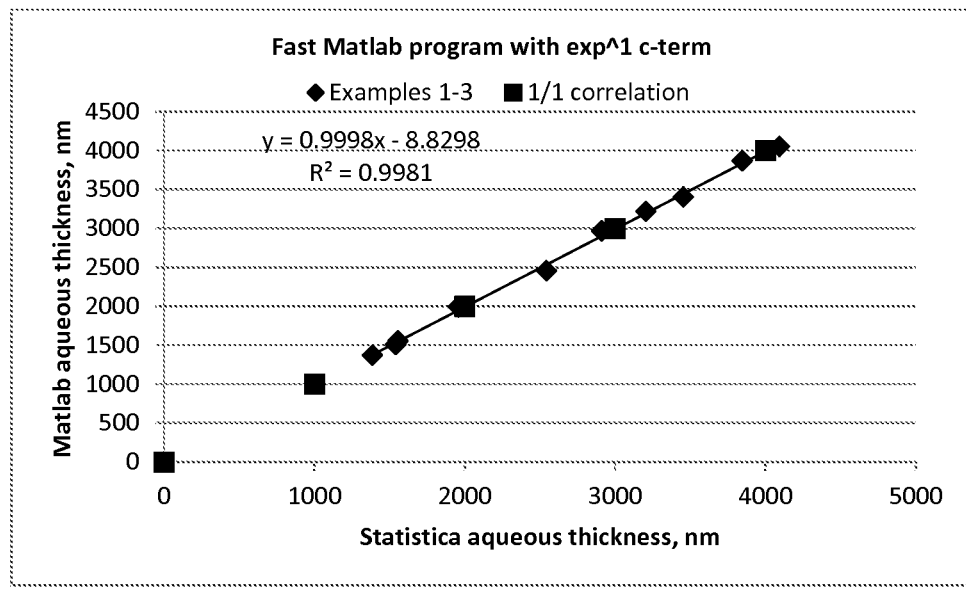
FIG. 13 shows the correlation between the tear film aqueous layer thickness values obtained using the methods of the '293 patent with the methods from co-pending application Ser. No. 14/298,176 and those obtained using the present methods for the data from Examples 1-3.

FIG. 13 shows the correlation between the tear film aqueous layer thickness values obtained using the methods of the '293 patent with the methods from co-pending application Ser. No. 14/298,176 and those obtained using the present Matlab method aqueous layer thickness values for spectra from Examples 1-3. A very good correlation was found (slope=0.9998, intercept 8.8298 nm and $r^2=0.9981$).

TABLE 3

| Spectrum | Stat aq/lip inputs/match | Calc. time, sec | Stat aq nm | Stat lip nm | Stat aq + lip | Stat b |
|---|---|---|---|---|---|---|
| sub1#29 | 3453.51/24.19/same | 11.8 | 3453.51 | 24.19 | 3477.70 | 0.8265 |
| sub4#5 | 1956.79/24.83/same | 3.8 | 1956.79 | 24.83 | 1981.62 | 0.6836 |
| sub6#7 | 3845.97/67.07/same | 2.2 | 3845.97 | 67.07 | 3913.04 | 0.6762 |
| sub6base#84 | 3204/80/same | 2.4 | 3204.24 | 80.32 | 3284.56 | 0.2876 |
| sub2DE | original '557 method | 400 | | | | |
| sub2DE | 2542.95/79.67/close values | 3.0 | 2542.95 | 79.67 | 2622.62 | 1.0323 |
| sub3#15 | original '557 method | 206 | | | | |
| sub3#15 | 1555.7/41.84/close values | 2.0 | 1555.70 | 41.84 | 1597.54 | 1.0761 |
| sub3#56 | original '557 method | 361 | | | | |
| sub3#56 | 1386.26/42.00/close values | 2.8 | 1386.26 | 42.00 | 1428.26 | 1.2879 |
| sub12#93 | original '557 method | 475 | | | | |
| sub12#93 | 4092.98/30.66/close values | 21.9 | 4092.98 | 30.66 | 4123.64 | 1.2512 |

| Mlab lip nm | Mlab b | Mlab c | Mlab aq nm | Mlab nd | Mlab error | 567 Mlab calc time, sec |
|---|---|---|---|---|---|---|
| 34.7 | 0.9223 | 0.1958 | 3405.6 | 1.3328 | 8.17E−06 | 408; 402 |
| 37.0 | 0.7530 | 0.1850 | 1991.4 | 1.3382 | 2.40E−05 | 235 |
| 71.3 | 0.6526 | 0.0204 | 3870.1 | 1.3351 | 1.53E−05 | 137 |
| 93.5 | 0.2227 | −0.1119 | 3217.2 | 1.3369 | 1.83E−05 | 220; 156 |
| 108.6 | 0.6040 | −0.2663 | 2595.4 | 1.3348 | 2.11E−05 | 400 |
| 95.6 | 0.8629 | −0.0593 | 2457.3 | 1.3313 | 2.32E−05 | |
| 71.3 | 1.0142 | 0.2230 | 1546.4 | 1.3368 | 2.67E−05 | 206 |
| 64.4 | 1.1702 | 0.2650 | 1553.0 | 1.3366 | 2.89E−05 | |
| 64.5 | 1.2768 | 0.2084 | 1365.9 | 1.3295 | 1.87E−05 | 361 |
| 58.1 | 1.4258 | 0.2269 | 1371.7 | 1.3296 | 1.87E−05 | |
| 39.4 | 1.3000 | 0.1199 | 3883.3 | 1.3298 | 1.62E−05 | 475 |
| 38.3 | 1.3487 | 0.1345 | 4053.0 | 1.3341 | 1.69E−05 | |

Example 4

In one embodiment, the method of Example 1 was followed using the same interferometry spectra as shown in Table 3. A faster computer was used for the spectrum fits in this example, an Intel® Core™ i5-4300U CPU @ 1.90, 2.50 GHz with 4.00 GB RAM and a 64-bit operating system. In this embodiment the exponential term for the c-term multiplier of the Matlab program was changed from a first-order exponential to a second-order exponential (results shown in Table 4):

From *exp(−b(5).*(1000./L).^1.0)) in the new program herein for the mathematical function to *exp(−b (5).*(1000./L).^2.0)) (Note that this change is made on three program lines).

TABLE 4

| Spectrum | Stat aq/lip inputs/match | Calc. time, sec | Stat aq nm | Stat lip nm | Stat aq + lip | Stat b |
|---|---|---|---|---|---|---|
| RHIf8hr#20 | 1540.6/31.53/close values | 2.4 | 1540.62 | 31.53 | 1572.15 | 0.0238 |
| sub3#15 | 1555.7/41.84/close values | 2.5 | 1555.70 | 41.84 | 1597.54 | 1.0761 |
| sub2DE | 2542.95/79.67/close values | 3.1 | 2542.95 | 79.67 | 2622.62 | 1.0323 |
| sub3#56 | 1386.26/42.00/close values | 1.8 | 1386.26 | 42.00 | 1428.26 | 1.2879 |
| sub6base#84 | 3204/80/close values | 1.9 | 3204.24 | 80.32 | 3284.56 | 0.2876 |
| sub4#5 | 1956.79/24.83/close values | 3.5 | 1956.79 | 24.83 | 1981.62 | 0.6836 |
| sub1#29 | 3453.51/24.19/close values | 3.7 | 3453.51 | 24.19 | 3477.70 | 0.8265 |
| sub21#43 | 2910.92/31.78/same | 7.8 | 2910.92 | 31.78 | 2942.70 | 0.3701 |
| sub6#7 | 3845.97/67.07/same | 2.2 | 3845.97 | 67.07 | 3913.04 | 0.6762 |
| sub12#93* | 4092.98/30.66/close values | 3.2 | 4092.98 | 30.66 | 4123.64 | 1.2512 |
| sub12#93** | 4092.98/30.66/close values | 3.4 | 4092.98 | 30.66 | 4123.64 | 1.2512 |

| Mlab lip nm | Mlab b | Mlab c | Mlab aq nm | Mlab nd | Mlab error |
|---|---|---|---|---|---|
| 47.0 | 0.0241 | 0.1146 | 1518.2 | 1.3630 | 1.09E−07 |
| 56.3 | 1.0413 | 0.0823 | 1561.9 | 1.3364 | 2.90E−05 |
| 99.4 | 0.8619 | −0.0336 | 2601.2 | 1.3348 | 2.11E−05 |
| 50.8 | 1.2829 | 0.0633 | 1379.9 | 1.3298 | 1.88E−05 |
| 84.2 | 0.2844 | 0.005 | 3222.2 | 1.3367 | 1.91E−05 |
| 17.8 | 0.6834 | −0.0288 | 2014.1 | 1.3377 | 2.74E−05 |
| 14.5 | 0.8188 | −0.0301 | 3429.6 | 1.3329 | 9.20E−06 |
| 16.1 | 0.3684 | −0.0773 | 2990.3 | 1.3357 | 2.88E−06 |
| 62.2 | 0.7345 | 0.0196 | 3874.9 | 1.3350 | 1.61E−05 |
| 19.3 | 1.2421 | −0.058 | 6131.5 | 1.3316 | 4.00E−06 |
| 38.4 | 1.3505 | 0.1369 | 3879.5 | 1.3298 | 1.61E−05 |

*poor fit;

**good fit with exp^1 for c-term

Figure 14:
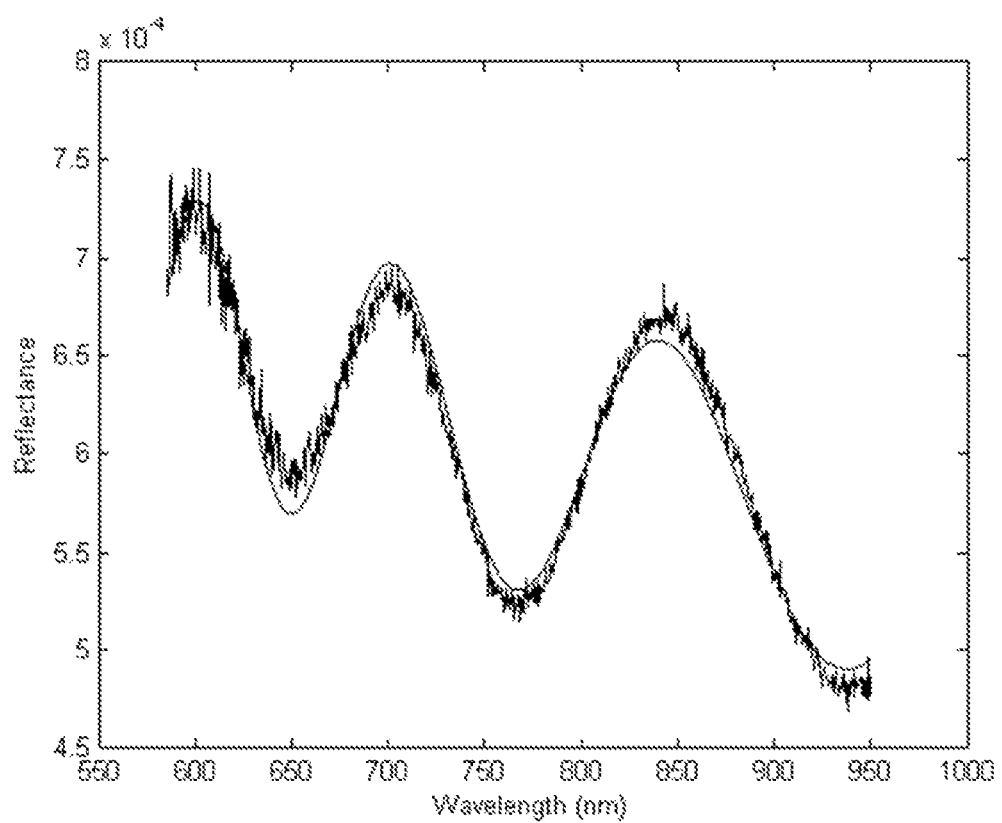
FIG. 14 shows the results of a curve-fitting procedure using a second-order exponential c-term.

It can be seen in Table 4 that, with the exception of a single spectrum, sub12#93, values close to those obtained in Table 3 were produced. FIG. 14 shows the results of the fit obtained for spectrum RHlf8hr#20 as an example for the usage of the second-order exponential c-term.

Figure 15:
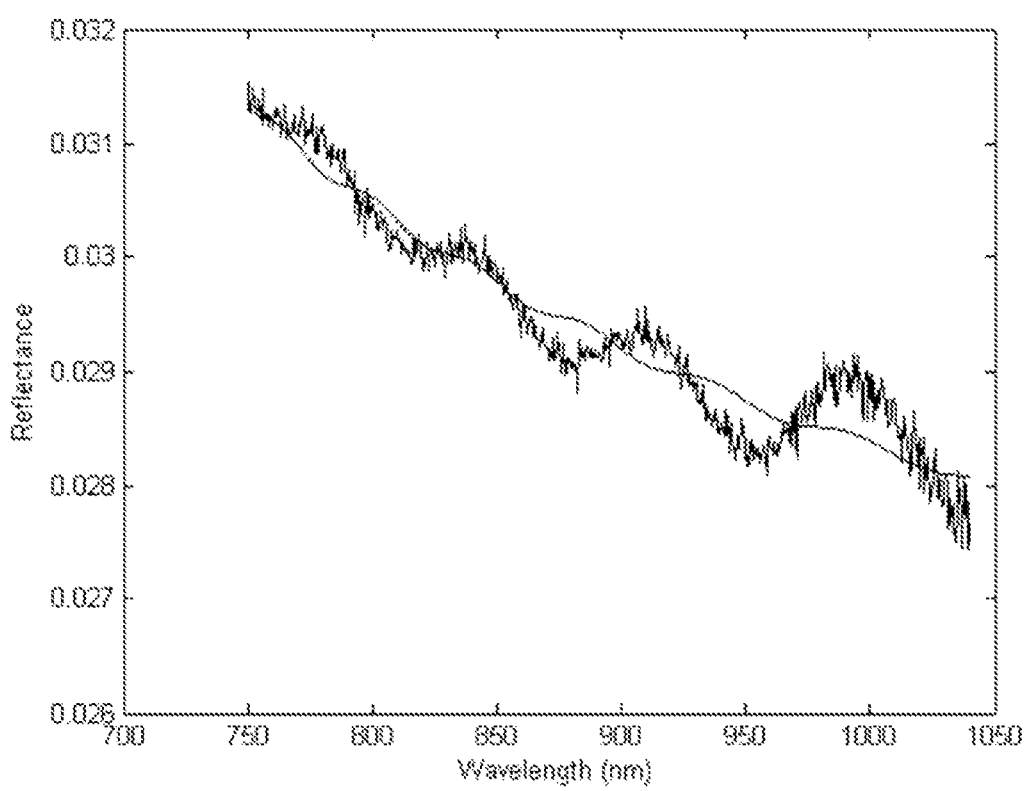
FIGS. 15 and 16 show spectra curve-fitted using a second-order (FIG. 15) or first-order (FIG. 16) exponential c-term.
Figure 16:
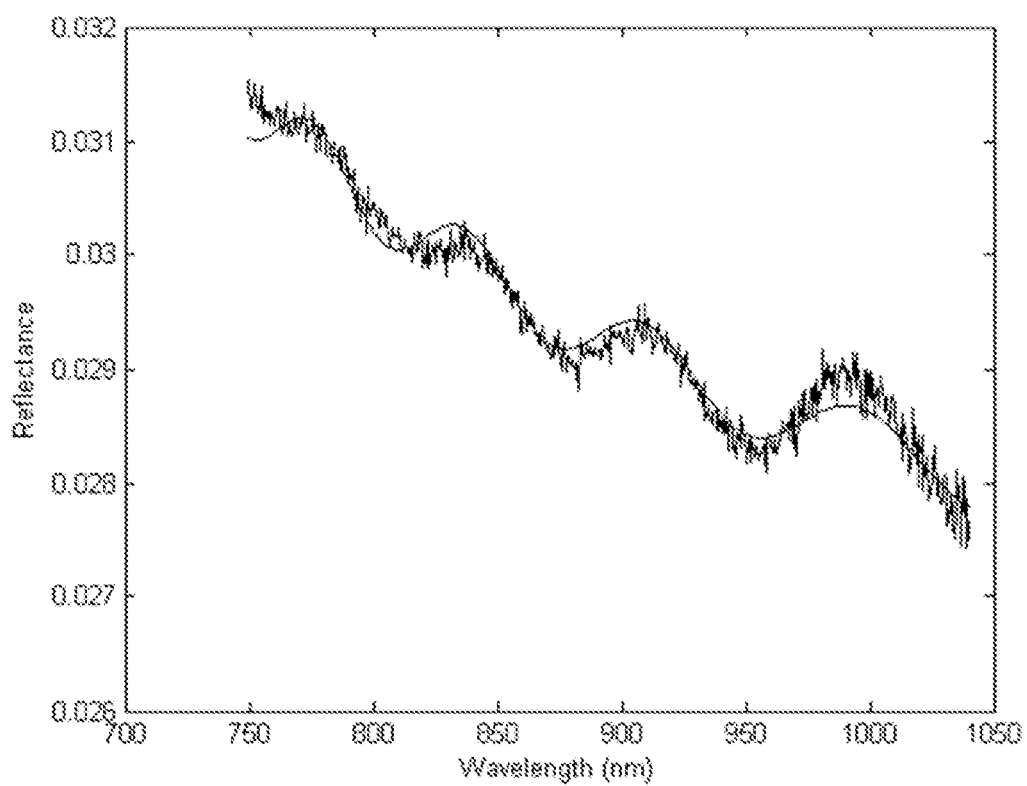

The present method Matlab program with a second-order exponential for the c-term achieved good fits for all other spectra in Table 4 (data not shown), with the exception of spectrum sub12#93. This is seen in comparing FIG. 15, showing the second order exponential c-term result, with FIG. 16, showing the first-order exponential c-term result. Thus, the second-order exponential c-term can be used as well as the first-order exponential c-term, with some exceptions.

Figure 17:
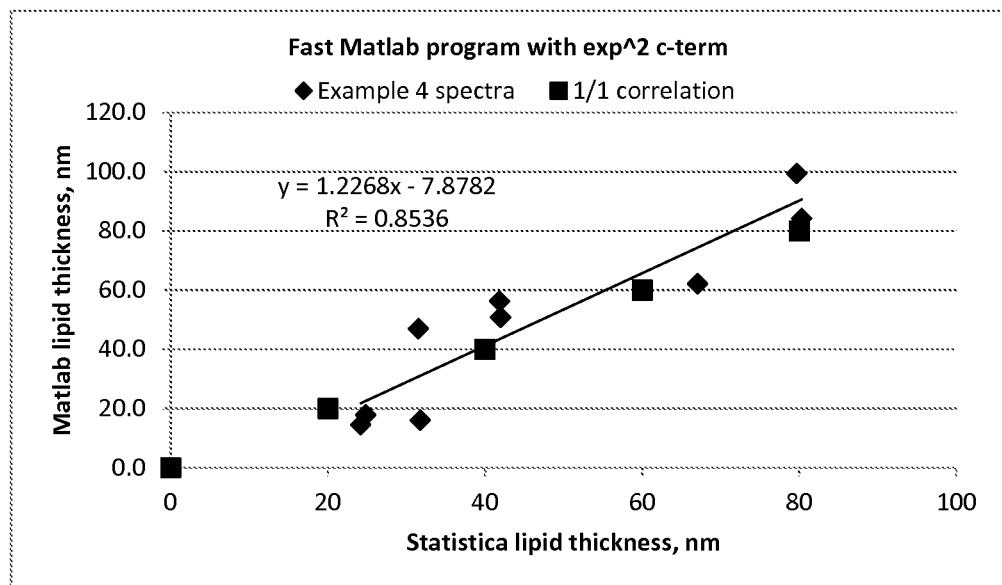
FIG. 17 shows the correlation between tear film lipid layer thickness values obtained using the methods of the tear film lipid layer thickness values using the methods from co-pending application Ser. No. 14/298,176 and those obtained using the present methods for spectra from Example 4, with the exception of spectrum sub12#93.

FIG. 17 shows the correlation between tear film lipid layer thickness values obtained using the methods of the tear film lipid layer thickness values using the methods from co-pending application Ser. No. 14/298,176 and those obtained using the present Matlab method lipid layer thickness values for spectra Examples 4, with the exception of spectrum sub12#93. A reasonably good correlation was again found (slope=1.2268, intercept 7.8782 nm and $r^2$=0.8536) given the nanometer measurement scale for the clinical interferometer and associated mathematics and software. The average difference found for the data set was 2.8 nm, as some Statistica values were higher and some were lower than the Matlab-fitted values for the same spectra.

Figure 18:
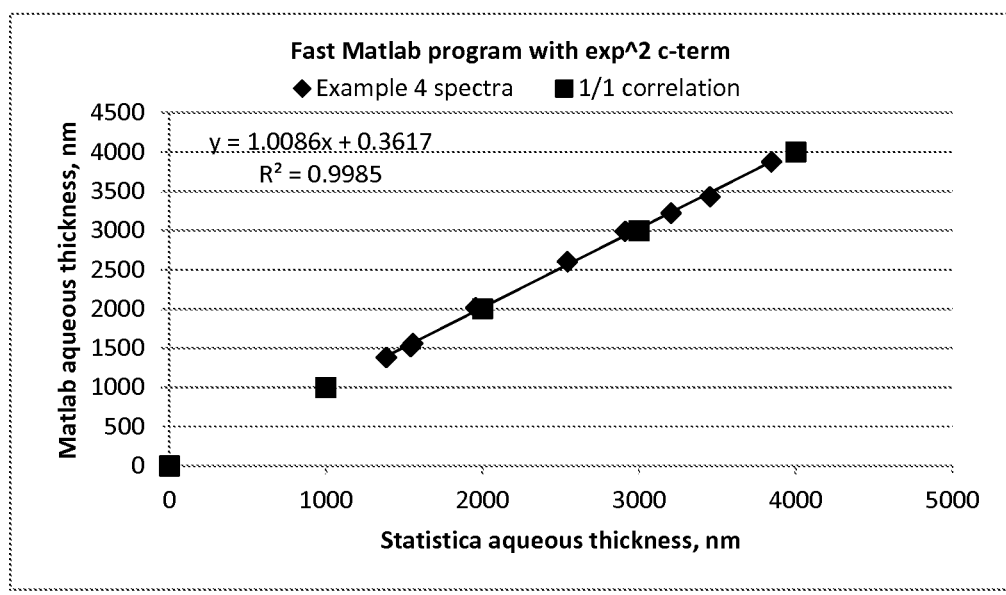
FIG. 18 shows the correlation between tear film aqueous layer thickness values obtained using the methods of the '293 patent with the methods from co-pending application Ser. No. 14/298,176 and those obtained using the present methods for spectra from Example 4.

FIG. 18 shows the correlation between tear film aqueous layer thickness values obtained using the methods of the '293 patent with the methods from co-pending application Ser. No. 14/298,176, and those obtained using the present Matlab method aqueous layer thickness values for spectra from Example 4. A very good correlation was found (slope=1.0086, intercept 0.3617 nm and $r^2$=0.9985).

The method of the present invention also includes methods wherein only one of the tear film aqueous or lipid layer thickness values derived from the Statistica program are used as input starting values, and the Matlab software is allowed to run the other 7× matrix calculations for lipid layer thickness (when aqueous thickness is input) or the 6× matrix calculations for aqueous layer thickness (when lipid thickness is input). Both of these alternative methods result in significantly improved shorter Matlab software program calculation times due to the reduced sizes of the calculation matrices.

In various embodiments, the disclosed methods may be carried out on a computing system in communication with an interferometer (e.g. a wavelength-dependent interferometer). The computing system may include one or more computer systems in communication with one another through various wired and wireless communication means which may include communications through the Internet and/or a local network (LAN). Each computer system may include an input device, an output device, a storage medium (including non-transient computer-readable media), and a processor such as a microprocessor. Possible input devices include a keyboard, a computer mouse, a touch screen, and the like. Output devices include a cathode-ray tube (CRT) computer monitor, a LCD or LED computer monitor, and the like. Storage media may include various types of memory such as a hard disk, RAM, flash memory, and other magnetic, optical, physical, or electronic memory devices. The processor may be any suitable computer processor for performing calculations and directing other functions for performing input, output, calculation, and display of data in the disclosed system. Implementation of the computing system may include generating a set of instructions and data that are stored on one or more of the storage media and operated on by a controller. Thus, one or more controllers may be programmed to carry out embodiments of the disclosed invention. The data associated with the system may include image data, numerical data, or other types of data.

Various features and advantages of the invention are set forth in the following claims.

What is claimed is:

1. A method for determining optical properties of a corneal region, comprising the steps of:
    obtaining a combined tear film aqueous layer plus lipid layer thickness;
    obtaining a tear film lipid layer thickness, wherein obtaining a tear film lipid layer thickness comprises
        measuring a tear film aqueous layer plus lipid layer relative reflectance spectrum using a wavelength-dependent optical interferometer,
        converting the measured tear film aqueous plus lipid layer relative reflectance spectrum to a calculated absolute reflectance spectrum, and
        determining a tear film lipid layer thickness using an iterative curve fitting procedure;
    subtracting the tear film lipid layer thickness from the combined tear film aqueous layer plus lipid layer thickness to obtain a tear film aqueous layer thickness; and
    determining a corneal layer refractive index based on the tear film lipid layer thickness and the tear film aqueous layer thickness.

2. The method of claim 1, wherein obtaining a combined tear film aqueous layer plus lipid layer thickness comprises measuring a tear film aqueous layer plus lipid layer relative reflectance spectrum using a wavelength-dependent optical interferometer.

3. The method of claim 1, wherein determining a corneal layer refractive index based on the tear film lipid layer thickness and the tear film aqueous layer thickness comprises a matrix fitting calculation based on the tear film lipid layer thickness and the tear film aqueous layer thickness.

4. The method of claim 3, wherein each of the lipid layer thickness and the aqueous layer thickness comprises an initial estimate and wherein the matrix fitting calculation determines a final lipid layer thickness and a final aqueous layer thickness.

5. The method of claim 4, wherein the matrix fitting calculation comprises finding a best fit curve for an observed a tear film reflectance spectrum obtained using a wavelength-dependent optical interferometer.

6. The method of claim 3, wherein the matrix fitting calculation comprises fitting the calculated absolute reflectance spectrum to a mathematical construct based upon a characteristic mathematical matrix of a plurality of thin film layers comprising in sequence, from top to bottom: air as a boundary, a tear film lipid layer, a tear film aqueous layer, and a corneal tissue as a semi-infinite substrate.

7. The method of claim 6, wherein the corneal tissue comprises an epithelium.

8. A system for determining optical properties of a corneal region, comprising:
    a wavelength-dependent optical interferometer; and
    a controller in communication with the interferometer, the controller configured to
        obtain a combined tear film aqueous layer plus lipid layer thickness, obtain a tear film lipid layer thickness, wherein in order to obtain a tear film lipid layer thickness, the controller is further configured to measure a tear film aqueous layer plus lipid layer relative reflectance spectrum using the wavelength-dependent optical interferometer, convert the measured tear film aqueous plus lipid layer relative reflectance spectrum to a calculated absolute reflectance spectrum, and determine a tear film lipid layer thickness using an iterative curve fitting procedure, subtract the tear film lipid layer thickness from the combined tear film aqueous layer plus lipid layer thickness to obtain a tear film aqueous layer thickness, and determine a corneal layer refractive index based on the tear film lipid layer thickness and the tear film aqueous layer thickness.

9. The system of claim 8, wherein the controller, in order to obtain a combined tear film aqueous layer plus lipid layer thickness, is further configured to measure a tear film aqueous layer plus lipid layer relative reflectance spectrum using the wavelength-dependent optical interferometer.

10. The system of claim 8, wherein the controller, in order to determine a corneal layer refractive index based on the tear film lipid layer thickness and the tear film aqueous layer thickness, is further configured to perform a matrix fitting calculation based on the tear film lipid layer thickness and the tear film aqueous layer thickness.

11. The system of claim 10, wherein each of the lipid layer thickness and the aqueous layer thickness comprises an initial estimate and wherein the matrix fitting calculation determines a final lipid layer thickness and a final aqueous layer thickness.

12. The system of claim 10, wherein the controller, to perform the matrix fitting calculation, is further configured to fit the calculated absolute reflectance spectrum to a mathematical construct based upon a characteristic mathematical matrix of a plurality of thin film layers comprising in sequence, from top to bottom: air as a boundary, a tear film lipid layer, a tear film aqueous layer, and a corneal tissue as a semi-infinite substrate.

13. The system of claim 12, wherein the corneal tissue comprises an epithelium.

14. The system of claim 13, wherein the controller, to perform the matrix fitting calculation, is further configured to find a best fit curve for an observed a tear film reflectance spectrum obtained using the wavelength-dependent optical interferometer.

* * * * *